(12) United States Patent
Klecker et al.

(10) Patent No.: US 6,682,715 B2
(45) Date of Patent: Jan. 27, 2004

(54) NUCLEOSIDES FOR IMAGING AND TREATMENT APPLICATIONS

(75) Inventors: Raymond W. Klecker, Silver Spring, MD (US); Lawrence Anderson, Wheaton, MD (US); Aspandiar G. Katki, Gaithersburg, MD (US); Jerry M. Collins, Rockville, MD (US)

(73) Assignee: The United States of Americas as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/941,721

(22) Filed: Aug. 30, 2001

(65) Prior Publication Data

US 2003/0049201 A1 Mar. 13, 2003

Related U.S. Application Data

(62) Division of application No. 09/530,276, filed as application No. PCT/US98/23109 on Oct. 30, 1998.
(60) Provisional application No. 60/063,587, filed on Oct. 30, 1997.

(51) Int. Cl.[7] .................. A61K 51/00; A01N 61/00; A01N 43/04; C07H 21/02
(52) U.S. Cl. .................. 424/1.11; 514/1; 514/44; 536/25.3
(58) Field of Search ............. 514/1, 44; 536/25.3; 424/1.11

(56) References Cited

U.S. PATENT DOCUMENTS

| 5,241,060 A | 8/1993 | Engelhardt et al. |
| 5,466,786 A | 11/1995 | Buhr et al. |

(List continued on next page.)

FOREIGN PATENT DOCUMENTS

| WO | WO 99/08110 | 2/1999 |
| WO | WO 99/32113 | 7/1999 |

(List continued on next page.)

OTHER PUBLICATIONS

Qing, Li et al. "A Novel Approach to Thymidylate Synthase as a Target for Cancer Chemotherapy", *Molecular Pharmacology*, vol. 59, No. 3. pp. 446–452, 2001.

(List continued on next page.)

*Primary Examiner*—Jezia Riley
(74) *Attorney, Agent, or Firm*—Venable LLP; Keith G. Haddaway

(57) ABSTRACT

Methods of diagnosing and/or of treating tumors by administering a nucleoside analog which is activated by thymidylate synthase and/or thymidine kinase enzyme into a diagnostic or toxic metabolite, and uridine analog compounds, and compositions of same having a pharmaceutically acceptable carrier. For diagnostic applications, compounds containing a label and methods of use of such compounds are described.

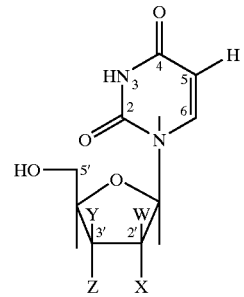

12 Claims, 7 Drawing Sheets

U.S. PATENT DOCUMENTS

| | | | |
|---|---|---|---|
| 5,741,900 A * | 4/1998 | Gmeiner et al. ......... 536/25.31 |
| 5,879,661 A | 3/1999 | Conti et al. |
| 6,159,706 A | 12/2000 | Shepard |
| 6,245,750 B1 | 6/2001 | Shepard |
| 6,331,287 B1 | 12/2001 | Conti et al. |
| 6,339,151 B1 | 1/2002 | Shepard et al. |
| 2001/0016329 A1 | 8/2001 | Shepard |
| 2001/0034440 A1 | 10/2001 | Shepard et al. |

FOREIGN PATENT DOCUMENTS

| | | |
|---|---|---|
| WO | WO 99/35292 | 7/1999 |
| WO | WO 99/37753 | 7/1999 |
| WO | WO 01/07087 | 2/2001 |
| WO | WO 01/07088 | 2/2001 |
| WO | WO 01/07454 | 2/2001 |
| WO | WO 01/64687 | 9/2001 |
| WO | WO 01/83492 | 11/2001 |

OTHER PUBLICATIONS

Abstract No. 1594—Christopher R. Boyer, Patricia L. Karjian, Geoffrey M. Wahl, Saskia T.C. Neuteboom; Nucleoside Transport Inhibitors, Dipyridamole and P–Nitrobenzylthioinosine, Selectively Potentiate the Activity of NB1011 against Human Tumor Cell Lines Expressing High Levels of Thymidylate Synthase; On–line Publication date Feb. 27, 2001.

Abstract No. 2731—0 Christopher R. Boyer, Qing Li, Patricia L. Karjian, Jean Lee, Geoffrey M. Wahl, Saskia T.C. Neuteboom; NB1011, a Novel Drug That Targets Tumor Cells Overexpressing Thymidylate Synthase, Induces p21, BAX and GADD45 and Blocks G2/M Cell Cycle Progression in MCF7TDX Cells; On–line Publication date Feb. 27, 2001.

Abstract No. 1581—Julie L. Eiseman, Raymond W. Klecker, Clive Brown–Proctor, Deborah R.Hamburger, Su–Shu Pan, Merrill J. Egorin, Jerry M. Collins; Preclinical Studies Evaluating 2'F–Ara–Deoxyuridine (FAU) As A Prodrug and Positron Emission Tomography (PET) Probe for Thymidylate Synthase.; On–line Publication date Feb. 27, 2001.

Wang, Hui et al. "Radiolabeled 2'–fluorodeoxyuracil–β–D–arabinofuranoside (FAU) and 2'–fluoro–5–methyldeoxyuracil–β–D–arabinofuranoside (FMAU) as tumor–imaging agents in mice", *Cancer Chemother Pharmacol*, 49: 419–424 (2002).

B. Chandrasekaran et al.: "Deoxypyrimidine–induced Inhibition of the Cytotoxic Effects of 1–B–D–arabinofuranosyluracil." Cancer Chemother. Pharmacol., vol. 29, No. 6, 1992, pp. 455–460.

J. Balzarini et al.: "Incorporation of 5–Substituted Pyrimidine Nucleoside Analogues into DNA of a Thymidylate Synthetase–Deficient Murine FM3A Carcinoma Cell Line." METH. and FIND. EXPTL. CLIN. PHARMACOL., vol. 7, No. 1, 1985, pp. 19–28.

T–S. LIN et al.: "Synthesis and biological Activity of 5–(Trifluoromethyl)–and 5–(Pentafluoroethyl) pyrimidine Nucleoside Analogues." Journal of Medicinal Chemistry., vol. 26, No. 4, 1983, pp. 598–601, American Chemical Society. Washington., US ISSN: 0022–2623.

R. Roots et al.: "Comparative Radiotoxicity of 3H–IudR and 125IudR After Incorporation into DNA of Cultured mammalian Cells", Third Symposium on Microdosimetry, vol. 1, 1972, pp. 371–388.

X–B Kong et al.: "Cell Differentiation Effects of 2'–Fluoro–1–B–D–Arabinofuranosyl Pyrimidines in HL–60 Cells." Leukemia Research, vol. 11, No. 11, 1987, pp. 1031–1039.

L. Novotny et al.: "Structure–intestinal Transport and Structure–metabolism Correlations of some Potential Cancerostatic Pyrimidine Nucleosides in isolated Rat Jejunum." Cancer Chemother Pharmacol, vol. 13, No. 3, 1984, pp. 195–199.

M.S. Chen et al.: "Quantitative Determination of Antiviral Nucleoside Analog in DNA." Analytical Biochemistry, vol. 156, 1986, pp. 300–304.

Balzarini et al. Strategies for the Measurement of the Inibitory Effects of Thymidine Analogs on the Activity of Thymidylate Synthase In Intact Murine Leukemia L1210 Cells Biochiomica et Biophysica Acta vol. 785, 1984, pp. 36–45.

Yamana et al. Synthesis of Oligonucleotide Derivatives with Pyrene Group at Sugar Fragment, Tetrahedron Letters, vol. 32, pp. 6347–6350, 1991.

* cited by examiner

NUCLEOSIDES FOR IMAGING AND TREATMENT APPLICATIONS

CROSS REFERENCE TO RELATED APPLICATIONS

This application is a divisional application of application number 09/530,276, filed Apr. 28, 2000; which is a national stage application of International Patent Application No. PCT/US98/23109, filed Oct. 30, 1998; which claims the priority of U.S. Application No. 60/063,587, filed Oct. 30, 1997.

BACKGROUND OF THE INVENTION

1. Field Of The Invention

The present invention relates to methods, compounds, and compositions for diagnosing and/or treating tumor cells with anti-tumor agents activated by thymidylate synthase (TS) and/or thymidine kinase (TK). In addition, the present invention relates to the preparation and use of positron emitting nucleoside analogues for use in imaging applications. The nucleoside analogues used in imaging applications may be of the type activated by TS or, in other embodiments, may not require activation by TS. More particularly, the present invention relates to methods for diagnosing and/or treating tumor cells by administration of compounds such as nucleoside analogue prodrugs and related compounds or compositions containing these in an effective amount to identify susceptible tumors in biopsy specimens or via external imaging, and then proceeding to reduce or inhibit the replication or spread of tumor cells.

2. Technology Review

Thymidylate synthase (TS) is an essential enzyme for DNA synthesis. It is, however, more abundant in tumor cells than in normal tissues. For decades, research and clinical studies have been directed towards inhibition of TS in order to shrink tumors. In some instances, this strategy has been modestly successful, for example, fluorouracil and floxuridine are utilized in the treatment of breast, colon, pancreas, stomach, ovarian, and head/neck carcinomas as disclosed by Chu E, Takimoto C H. "Antimetabolites." In: DeVita V T Jr., Hellman S, Rosenberg S A, editors, *Cancer: Principles and Practice of Oncoloy*, Vol 1. 4th ed. Philadelphia: Lippincott, 1993:358–374.

Unfortunately, most tumors are inherently resistant to this strategy, and even those tumors, which are initially sensitive, develop resistance during the course of treatment as reported by Swain S M, Lippman M E, Egan E F, Drake J C, Steinberg S M, Allegra C J, in "Fluorouracil and High-Dose Leucovorin in Previously Treated Patients with Metastatic Breast Cancer," *J. Clin. Oncol,* 1989; 7:890–9. Recent applications of molecular probes for TS have demonstrated a consistent relationship between resistance and high expression of TS as noted in the following articles: Johnston P G, Mick R, Recant W, Behan K A, Dolan M E, Ratain M J, et al. "Thymidylate Synthase Expression and Response to Neoadjuvant Chemotherapy in Patients with Advanced Head and Neck Cancer", *J. Natl. Cancer Inst.* 1997; 89:308–13; Lenz H J, Leichman C G, Danenberg K D, Danenberg P V, Groshen S, Cohen H, Laine L, Crookes P, Silberman H, Baranda J, Garcia Y, Li J, Leichman L, "Thymidylate Synthase mRNA Level in Adenocarcinoma of the Stomach: A Predictor for Primary Tumor Response and Overall Survival", *J. Clin. Oncol.* 1996; 14:176–82; Johnston P G, Lenz H J, Leichman C G, Danenberg K D, Allegra C J, Danenberg P V, Leichman L, "Thymidylate Synthase Gene and Protein Expression Correlate and Are Associated with Response to 5-Fluorouracil in Human Colorectal and Gastric Tumors", *Cancer Res* 1995; 55:1407–12; Leichman L, Lenz H J, Leichman C G, Groshen S. Danenberg K, Baranda J, et al, "Quantitation of Intratumoral Thymidylate Synthase Expression Predicts for Resistance to Protracted Infusion of 5-Fluorouracil and Weekly Leucovorin in Disseminated Colorectal Cancers: Preliminary Report from an Ongoing Trial", *Eur. J. Cancer* 1995; 31:A 1305–10. Kornmann M, Link K H, Staib L., Danenberg P V., "Quantitation of Intratumoral Thymidylate Synthase Predicts Response and Resistance to Hepatic Artery Infusion with Fluoropyrimidines in Patients with Colorectal Metastases", *Proc. AACR* 38:614,1997.

A new generation of drugs designed to inhibit TS is reported by Touroutoglou N, Pazdur R. in "Thymidylate Synthase Inhibitors", *Clin. Cancer Res.* 1996; 2:227–43, to be currently in final stages of clinical testing. Despite the enormous resources which are being expended to improve the effectiveness of first-generation TS inhibitors, neither the existing drugs nor this new set of compounds are effective in tumors which have a high level of TS activity. Presently, once a tumor has become resistant due to-high levels of TS, there is no specific therapy available.

Instead of inhibiting TS, the present inventors hypothesized that is was possible to use this enzyme to activate uridine analogue prodrugs into more toxic thymidine analogues. The present inventors have previously demonstrated in *Molecular Pharmacology,* 46: 1204–1209, (1994) in an article entitled, "Toxicity, Metabolism, DNA Incorporation with Lack of Repair, and Lactate Production for 1–2'Fluoro-2'deoxy-β-D-arabinofuranosyl)-5-iodouracil (FIAU) in U-937 and MOLT-4 Cells" that 1-(2'Fluoro-2'deoxy-β-D-arabinofuranosyl)-uracil (FAU) was phosphorylated intracellularly by intact U-937 and MOLT-4 cells to FAU monophosphate (FAUMP), converted to its methylated form, 5-methyl-FAUMP (FMAUMP), and incorporated into DNA. These prior observations suggested that FAU would be an appropriate prototype for testing the cytotoxic potential of TS-activated prodrugs. It is to be understood that the former study produced data for different purposes and does not directly address the present discovery. To demonstrate the validity of the present concept, the inventors: (1) determined that TS is the enzyme which catalyzed the methylation; (2) examined the net formation rates of methylated species in a variety of cells; and (3) correlated the net formation rates of methylated species with cytotoxic effects.

Among pyrimidine nucleosides, 2'-deoxyuridine (dUrd) analogues are less toxic than their corresponding thymidine (dThd) analogues as indicated by Kong X B, Andreeff M, Fanucchi M P, Fox J J, Watanabe K A, Vidal P, Chou T C, in "Cell Differentiation Effects of 2'-Fluoro-1-beta-D-arabinofuranosyl Pyrimidines in HL-60 Cells." *Leuk Res,* 1987;11:1031–9. The present inventors theorized that following entry into the cell and phosphorylation, an analogue of dUrd would serve as a selective prodrug if TS can methylate it to generate the corresponding dThd analogue. Thus, tumors which are resistant to TS inhibitors, because of high levels of TS, would be particularly sensitive to these deoxyuridine (dUrd) analogues, because they would be more efficient in producing the toxic thymidine (dThd) species. This strategy is completely novel, since it is entirely different from all prior approaches towards TS as an anti-tumor target. Contrary to previous research and clinical studies which are directed towards the inhibition of TS in order to shrink tumors, the present invention utilizes TS to activate uridine analogue prodrugs into the more toxic thymidine analogues to reduce or inhibit tumor cells, especially tumor cells which are inherently resistant to or develop resistance to existing therapies. The present invention is additionally highly complementary to all prior approaches towards inhibition of TS as an antitumor target.

Further, because success of therapy with drugs such as FAU or its analogues is related to extent of incorporation into DNA, the analysis of DNA can provide diagnostic information regarding the optimal therapy for a tumor. Thus, by examining a biopsy specimen of tumor, or by externally imaging tumors, it can be predicted whether therapy with FAU or related compounds would be successful, or whether alternate therapy should be used.

In addition to assessing tumor therapy, there are a variety of other medical circumstances in which it is important to determine the proliferation rate (growth) of cells within a particular tissue in the body. These include: assessment of bone marrow function (e.g., after transplantation and/or stimulation with growth factors), regeneration of the liver following surgery or injury, and expression of enzyme function following gene therapy.

Traditional approaches to determine growth rate have been invasive; i.e., have required obtaining a biopsy from the patient. In addition to the discomfort and risks associated with biopsy procedures, only a small sample of tissue is obtained. Thus, biopsies carry the inherent risk of misdiagnosis as the small sample may not be representative of the entire region. Thus, there is a need in the art for other methodologies to determine the growth rate of tissues.

Non-invasive, external imaging methods avoid the need for biopsies, and also have the capability of scanning large areas of the body, indeed, the entire body if necessary. Since growth (proliferation) requires the synthesis of DNA from nucleosides, administration of nucleosides which have been radiolabeled with a positron emitter provides the ability to externally monitor events occurring within the body by use of imaging technologies such as a PET (Positron Emission Tomograph) scanner, or other photon-detecting devices such as SPECT (Single Photon Emission Computed Tomograph), or gamma cameras.

These imaging technologies are only limited by the availability of probes whose biological fates provide information as to the proliferative state of the tissue examined. Thymidine is a particularly useful probe for monitoring growth/DNA synthesis, because it is the only nucleoside for which direct incorporation of exogenously applied nucleoside into DNA is common by "salvage" pathways. There is no dependence upon the ribonucleotide pathways for the incorporation of thymidine. Thymidine itself is unsuitable as a probe in these imaging technologies, since the molecule is rapidly degraded in the body. Analogues of thymidine such as FMAU and FIAU are excellent imaging probes, because they: 1) completely follow thymidine pathways for incorporation into DNA; 2) are not degraded by catabolic enzymes; and 3) can be labeled with $^{18}F$, the most desirable atom for positron imaging.

Imaging probes incorporating other positron emitting moieties have been used in the prior art. For example, a synthesis for $^{11}C$-FMAU has been reported. However, there are a number of practical limitations dictated by the 20-minute half-life of $^{11}C$. Probe molecules containing $^{11}C$ must literally be prepared on-site and used within an hour. This requirement makes it unfeasible to have a regional preparation center and ship the molecules to surrounding medical facilities. Thus, every facility desiring to perform imaging studies using a $^{11}C$-labeled probe must have on site the cyclotron facilities to prepare the isotope. An additional limitation of $^{11}C$-containing labels arises when the biological phenomena requires more than an hour for full expression. The short half life of $^{11}C$ means that insufficient $^{11}C$ would remain to be imaged in these situations.

In addition to $^{11}C$-containing probes, probes labeled with $^{18}F$ are known in the prior art. $^{18}F$-fluorodeoxyglucose (FDG), a currently employed imaging probe, is synthesized and distributed from a regional facility making it more easily available for imaging purposes. Further, nucleoside analogues incorporating $^{18}F$ in positions other than those of the present invention, for example $^{18}F$ at the 5 position of uracil, have been reported.

Notwithstanding the existence of the probe molecules discussed above, there exists a need in the art for probe molecules for use in external imaging technologies. In addition, a need remains in the art for additional therapeutic modalities for the treatment of cell proliferation disorders. These and other needs have been met by the present invention.

SUMMARY OF THE INVENTION

The present invention provides compounds, compositions, and methods of diagnosing and/or treating tumors. The compounds of the present invention include nucleoside analogues which are activated by thymidylate synthase and/or thymidine kinase enzymes in an effective amount for diagnosis or to reduce or inhibit the replication or spread of tumor cells. These compounds and compositions comprising these compounds are easily administered by different modes known in the art and can be given in dosages that are safe and provide tumor inhibition at the relevant sites.

The present invention includes nucleoside analogues containing a positron emitting label moiety for use in imaging applications. These analogues may be synthesized so as to require activation by TS prior to incorporation into DNA and subsequent imaging. In alternative embodiments, the analogues of the present invention will not require activation by TS when used for imaging applications. In other embodiments, the analogues may be used for imaging applications even though not incorporated into DNA.

Accordingly, it is the object of the present invention to provide compounds, compositions, and methods to identify susceptible tumors in biopsy specimens or via external imaging, and/or inhibit or reduce the replication or spread of tumor cells.

It is another object of the present invention to provide a treatment for tumors and other diseases characterized by abnormal cell proliferation by administrating these compounds or compositions either alone or in combination with other agents that inhibit tumor growth and/or with other classes of therapeutics used to treat such diseases.

It is another object of the present invention to assess the impact of other treatments (e.g., by radiotherapy or other drugs) upon tumor growth. In preferred embodiments, the treatments will be drugs intended to inhibit thymidylate synthase.

It is an object of the present invention to provide compounds and methods useful for external imaging applications. In preferred embodiments, the invention includes the selection, preparation, and uses of nucleosides labeled with fluorine-18 ($^{18}F$), a positron emitter. The methods of the present invention permit treatment individualization using surrogate markers such as external imaging. Other embodiments of the invention may be useful in selecting the most effective drugs to be used against tumors in humans.

It is an object of the invention to provide a method that can be utilized to monitor and assess the efficacy of supportive treatments. In preferred embodiments the supportive treatments may be bone marrow transplant and/or stimulation by growth factors. In other preferred embodiments, the present invention may be used to monitor and assess the course of liver regeneration after surgery or injury.

It is an object of the present invention to provide a method for monitoring the expression of genes introduced in gene therapy applications.

Other features and advantages of the present invention will be apparent from the following description of preferred embodiments. These and other objects, features and advantages of the present invention will become apparent after a review of the following detailed description and claims.

DETAILED DESCRIPTION OF THE INVENTION

Tumor cells with high levels of thymidylate synthase (TS) represent a common therapeutic challenge for which no treatment strategy is currently available. One aspect of the present invention is that the growth of tumor cells with high TS can be preferentially inhibited with a uridine and/or a deoxyuridine (dUrd) analogue. As used hereinafter, uridine analogue is seen to include uridine and deoxyuridine and derivatives of both. Further, since tumors can vary widely, the identification of tumor cells with high levels of TS provides diagnostic information to select appropriate therapy for individual tumors. Using FAU as a prototype this concept has been successfully demonstrated.

The following SCHEME I illustrates the generalized structure for dUrd analogues and their intracellular activation pathways. For the endogenous nucleoside, dUrd, W=H. FAU has the substitution, W=F. A phosphate group is attached to the sugar at the 5'-position by thymidine kinase (TK) to form dUMP or its analogue, FAUMP. Subsequently, TS attaches a methyl group at the 5-position of the base to generate thymidylate, dTMP, or its analogue, FMAUMP.

SCHEME I

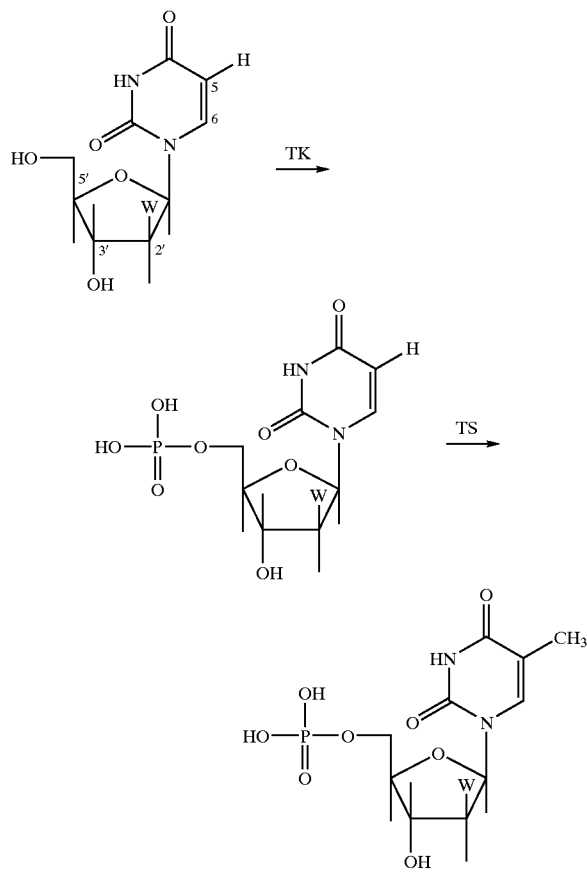

The present inventors demonstrated that FAU was converted into FMAU nucleotides and incorporated as FMAU into cellular DNA. In particular, the monophosphate of FAU, FAUMP was converted by TS in cell extracts to the corresponding dThd form, FMAUMP. Incubation of FAU with tumor cell lines in culture inhibited their growth to a variable extent, depending upon the efficiency of activation via TS. This is the first demonstration that cells with high levels of TS activity can be more vulnerable to therapy than cells with low TS activity.

Figure 2A:
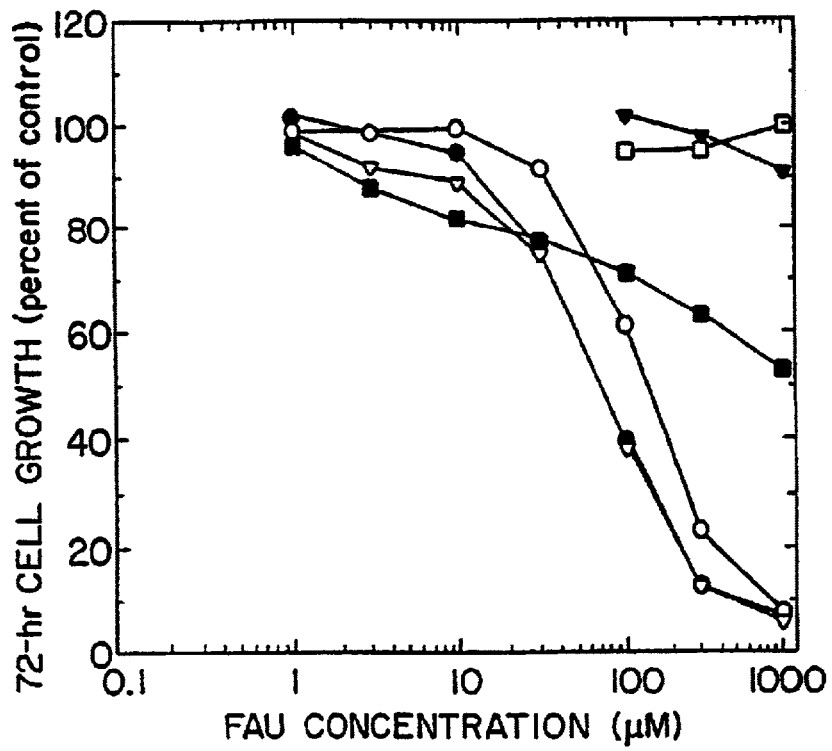
FIG. 2 graphically depicts the effect on cell growth of 72-hr continuous exposure to: (A) FAU, or (B) FMAU.
Cell designations:
CEM=●; MOLT-4=○; RAJI=▼; U-937=▽; K-562=■;
L1210=□.
Figure 2B:
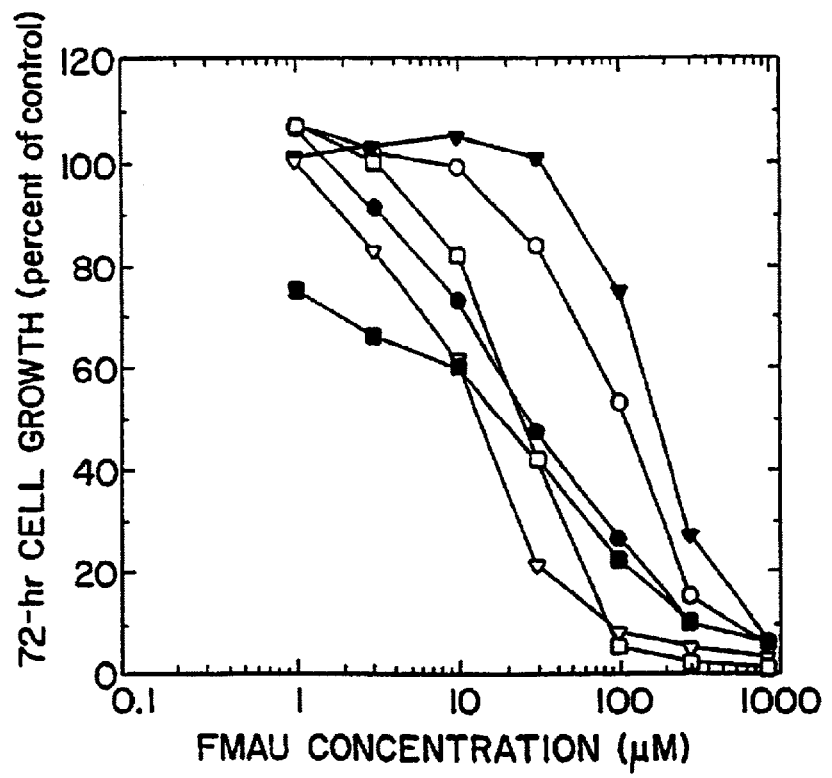
Figure 3A:
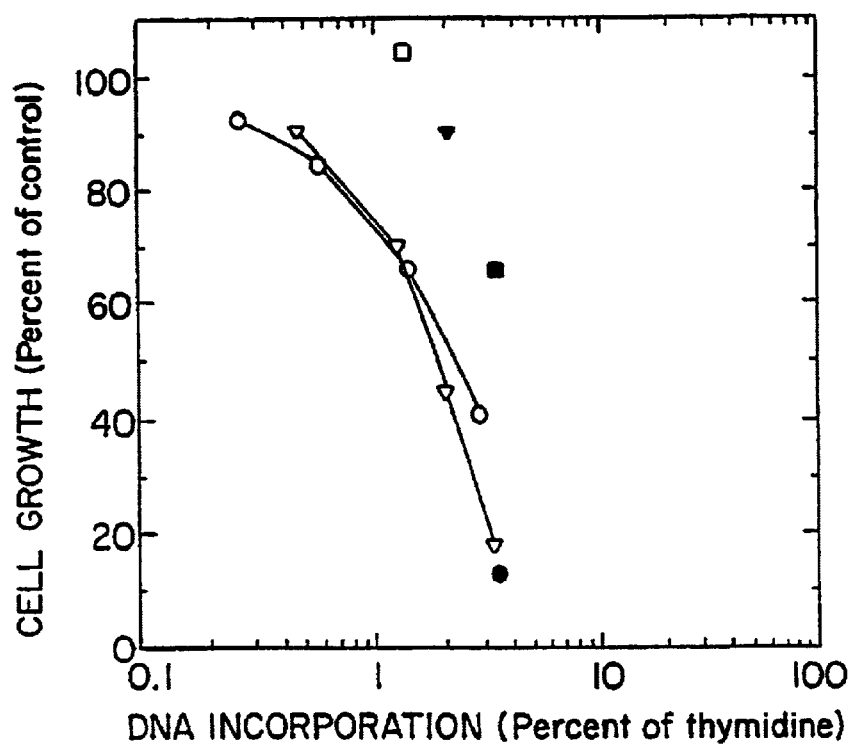
FIG. 3 graphically depicts the association of DNA incorporation with effect on cell growth. (A) FAU, (B) FMAU.
CEM=●; MOLT-4=○; RAJI=▼; U-937=▽; K-562=■;
L1210=□
Figure 3B:
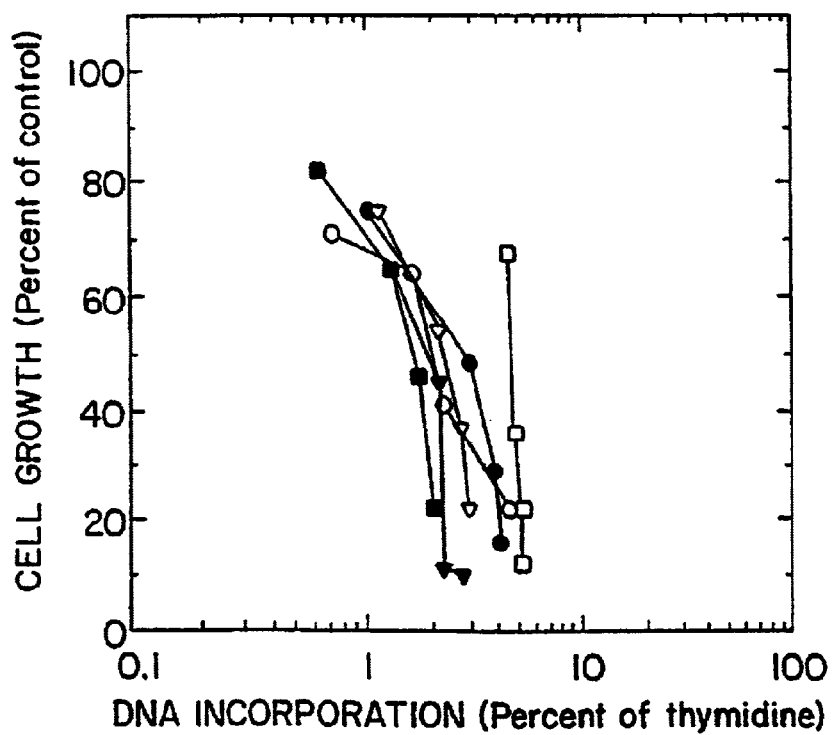

Wide variation among cell lines was observed in growth inhibition, and also relatively shallow slopes for the response versus extracellular concentration curves (FIGS. 2A, 2B). As a consequence, extracellular concentration of FMAU or especially FAU was a weak predictor of cytotoxicity, In contrast, the variation among cell lines in IC50 related to % replacement of dThd in DNA by FMAU was quite small (FIG. 3). Further, there were steep response curves for growth inhibition versus incorporation of drug (as FMAU) into DNA. Further, there was similarity among cell lines in toxicity at similar values for % replacement of dThd in DNA by FMAU. Thus, for equal exposure to the prodrug, selective toxicity could be related to differences in the rate of conversion to dThd analogues by TS. However, although conversion by TS is a necessary condition for toxicity, it is not sufficient. Opportunistic utilization of elevated TS activity also relies upon other steps, especially kinases and polymerases, as well as competition with endogenous synthesis. Growth inhibition ultimately depends upon the net action of all the pyrimidine pathways.

These data in FIG. 3 also demonstrate a use of deoxyuridine analogues for diagnostic applications. Tumors with high uptake of FAU and incorporation into DNA after methylation via thymidylate synthase could be imaged externally, e.g., by use of $^{18}$F-labeled FAU with positron emission tomography (PET). Alternatively, a dose of FAU could be administered prior to a tumor biopsy, and incorporation into DNA determined with the same techniques used for the cell culture samples in FIG. 3. By either modality, tumors with high DNA incorporation would be excellent candidates for therapy with FAU or related analogues, and tumors with low DNA incorporation should be treated with some other therapy.

Figure 4:
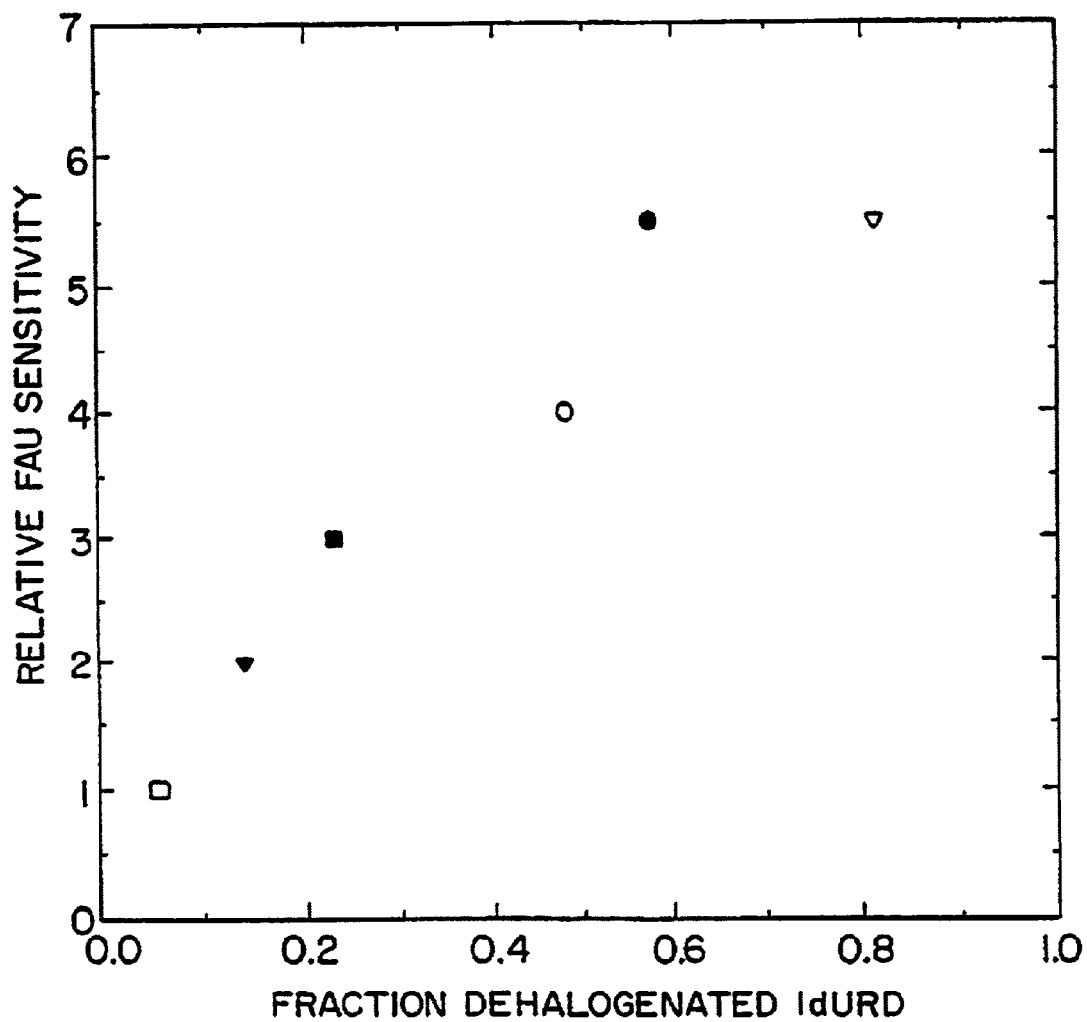
FIG. 4 graphically depicts the relative sensitivity of cell lines to growth-inhibition by FAU compared with the activation potential for TS, measured independently as relative dehalogenation of IdUrd. The most sensitive cell lines (U-937, CEM, MOLT-4) have 50or more dehalogenation. The least sensitive lines (Raji, L1210) have 15% or lower.
CEM=●; MOLT-4=○; RAJI=▼; U-937=▽; K-562=■;
L1210=□

It is possible that FAU has autonomous biologic effects separate from FMAU nucleotides. However, there were several indications that formation of FMAU by TS was sufficient to explain the majority of observed effects. In the present invention, comparison to the direct use of FMAU demonstrated that the toxic effects were dominated by FMAU nucleotides, especially similarity in DNA relationships. In addition, the relative sensitivity of cell lines to growth-inhibition by FAU was compared with the activation potential for TS, measured independently as relative dehalogenation of IdUrd (FIG. 4). The most sensitive cell lines (U-937, CEM, MOLT-4) have 50% or more dehalogenation. The least sensitive lines (Raji, L1210) have 15% or lower dehalogenation.

Nonetheless, under other experimental conditions, if there are differences among cells in transport, phosphorylation, or related pathways, then these factors can also influence response in addition to TS activity. A major advantage of imaging tumors with labeled FAU is that it detects the end-product of all these processes, which should translate into prognostic value.

Further, an alternative or additional approach to diagnosis is suggested by interpretation of the data in FIG. 4. Prior to biopsy, a dose of labeled IdUrd, either radiolabeled or more preferably labeled with stable isotopes, can be given to a patient. Dehalogenation can be determined from the DNA in the tumor biopsy and used to guide therapy.

The present invention provides a promising avenue of attack for common human tumors which have previously been resistant to therapeutic approaches. Although FAU was used to demonstrate the principle, FAU was not very potent, and may not necessarily be the optimal compound in its class. The rate of methylation by TS was rather low, only 1% compared with the endogenous substrate, dUMP. Despite this low rate, substantial amounts of FMAU were incorporated into DNA and toxicity was observed.

Figure 6A:
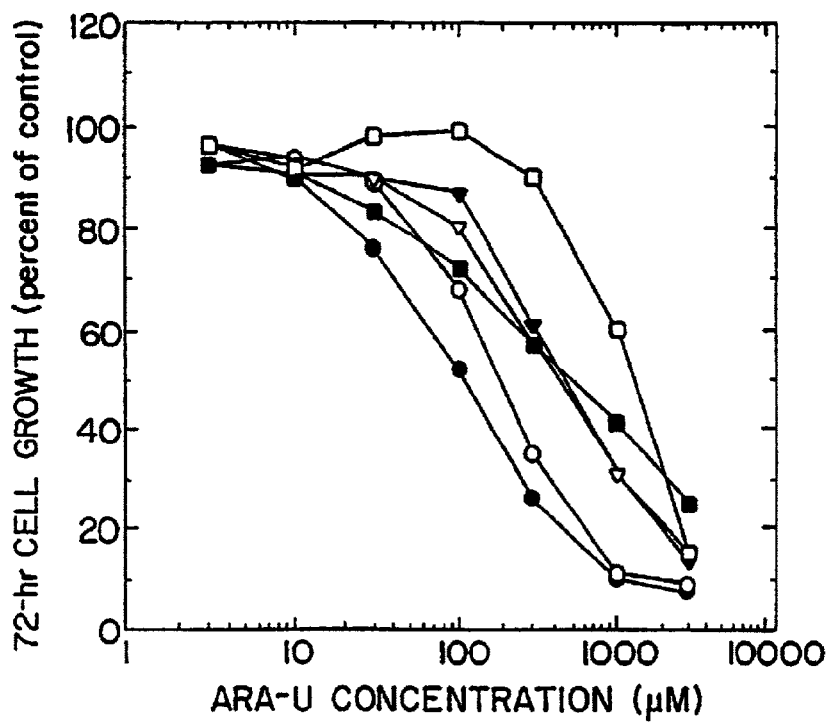
FIG. 6 graphically depicts effect on cell growth of 72-hr continuous exposure to: (A) ara-U, or (B) ara-T.
Cell designations:
CEM=●; MOLT-4=○; RAJI=▼; U-937=▽; K-562=■;
L1210=□
Figure 6B:
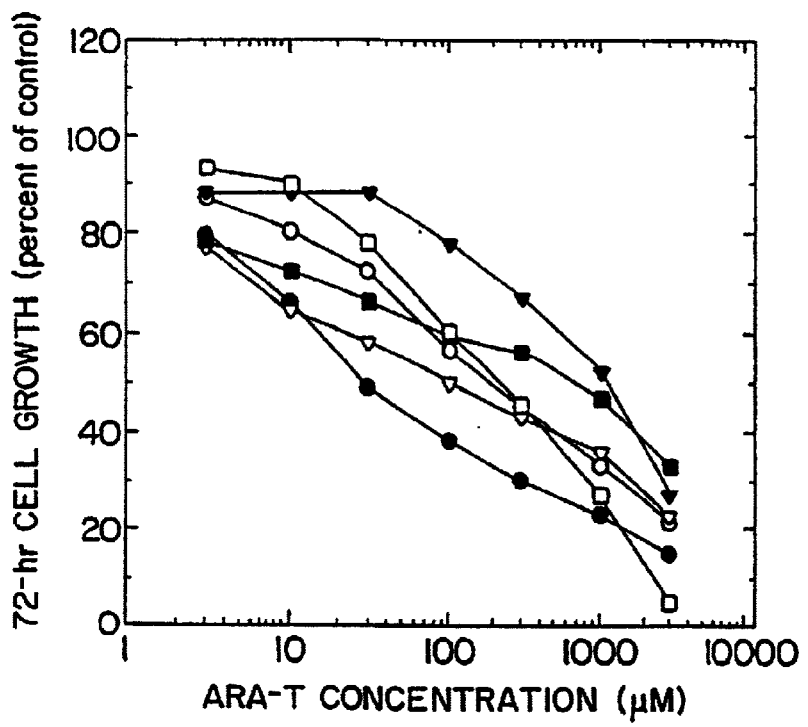
Figure 7A:
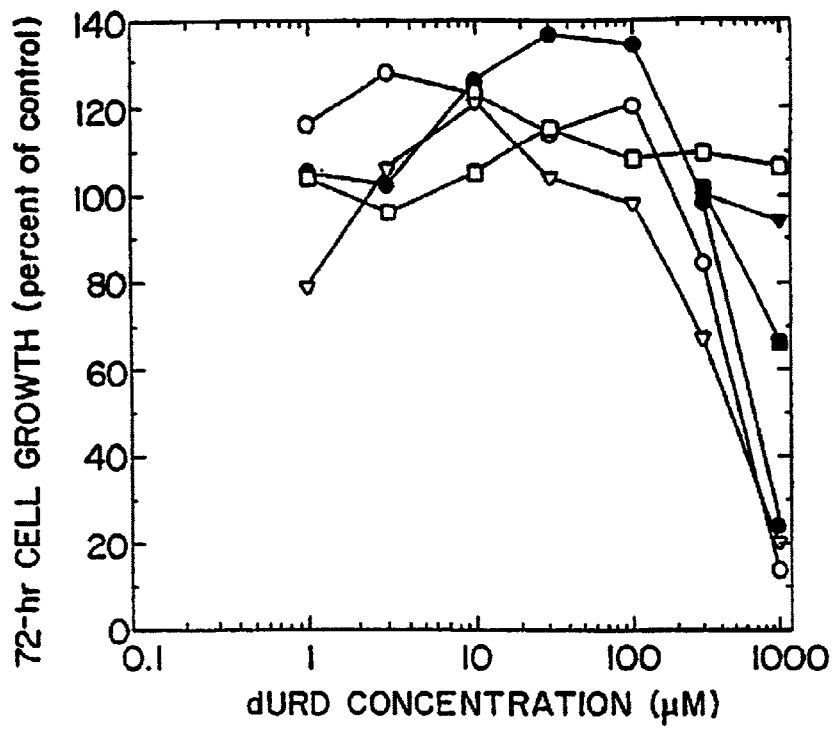
FIG. 7 graphically depicts effect on cell growth of 72-hr continuous exposure to: (A)dUrd, or (B) dThd.
Cell designations:
CEM=●; MOLT-4=○; RAJI=▼; U-937=▽; K-562=■;
L1210=□
Figure 7B:
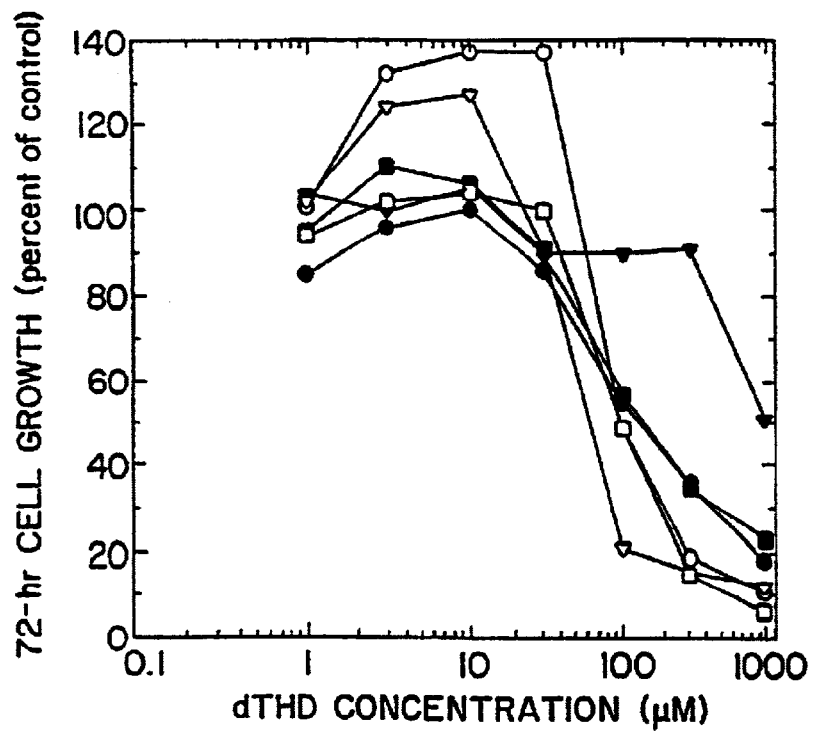

If FAU is not ideal, there are many other synthetic modifications of dUrd which can also serve as TS substrates. For example, cell culture data were obtained for uracil arabinoside (ara-U) and its methylated analogue, thymine arabinoside (ara-T). As shown in FIG. 6, the patterns of toxicity for ara-U and ara-T are very similar to those for FAU and FMAU in FIG. 2, suggesting a similar mechanism, i.e., methylation. Further, the endogenous compounds, deoxyuridine (dUrd) and thymidine (dThd) also display the same pattern of cell culture toxicity (FIG. 7).

Accordingly, the present invention includes compounds, compositions and method for diagnosis and treatment of tumors. One embodiment of the present invention is the use of uridine analogues or related compounds as disclosed herein to inhibit tumor formation. The present invention also includes compounds which have anti-tumor activity. The present invention also comprises a method of treating tumor formation in humans or animals comprising the steps of administering to the human or animal having tumors, a composition comprising an effective amount of a uridine analogue which is capable of inhibiting tumor growth.

It is common practice to treat tumors empirically without diagnostic information regarding the sensitivity of the specific tumor to a particular drug. Thus, FAU or related compounds could be used directly to treat tumors of a class known to have high levels of TS. Alternatively, therapy with FAU or related compounds could begin after failure of conventional TS inhibitors, with the inference that TS levels are elevated. A preferred approach would use biopsy or external imaging information to guide therapy selection, by diagnosing which tumors would be susceptible to FAU or related compounds, and which should use alternate approaches.

Tumor inhibiting and/or diagnosing compounds that can be used in accordance with the present invention include those having the following general formula:

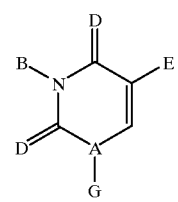

wherein:

A=N, C;

B=H, hydroxy, halogen, acyl ($C_1$–$C_6$), alkyl ($C_1$–$C_6$), alkoxy ($C_1$–$C_6$);

D=O, S, NH2;

E=H, alkyl, substituted alkyl, alkenyl, substituted alkenyl, alkoxy, substituted alkoxy, halogen, or any substituent which is readily cleaved in the body to generate any one of the before listed groups;

G=substituted or unsubstituted cyclic sugar, substituted or unsubstituted acyclic sugar, substituted or unsubstituted mono, di, or tri-phospho-cyclic-sugar phosphate; substituted or unsubstituted mono, di, or tri-phospho-acyclic-sugar phosphate; substituted or unsubstituted mono, di, or tri-phospho-cyclic sugar analogues, substituted or unsubstituted mono, di, or tri-phospho-acyclic sugar analogues wherein the substituents are alkyl ($C_1$ to $C_6$), alkoxy ($C_1$ to $C_6$), halogen.

The present invention also features methods of inhibiting tumor growth in mammals by administering a compound according to the above formula in a dosage sufficient to inhibit tumor growth.

The preferred compounds are:

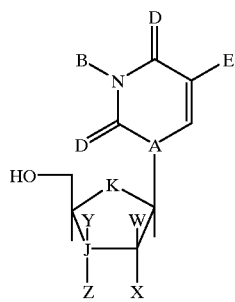

wherein:
A=N, C;
B=H, hydroxy, halogen, acyl ($C_1$–$C_6$), alkyl ($C_1$–$C_6$), alkoxy ($C_1$–$C_6$);
D=O, S, NH2;
E=H, ||',
W, X, Y, Z=H, hydroxy, halogen, alkyl ($C_1$–$C_6$), alkoxy ($C_1$–$C_6$), a label containing moiety or a label;
J=C, S; and
K=O, C.

In preferred embodiments for anti-tumor activity, E may be H,

In other preferred embodiments, W is a halogen. In a most preferred embodiment, W is Fluorine and E is H, methyl, iodine or a substituent readily cleaved by the body to generate one of these groups. However, other embodiments are within the scope of the present invention.

It is to be understood that the compounds of the present invention can exist as enantiomers and that the racemic mixture of enantiomers or the isolated enantiomers are all considered as within the scope of the present invention.

The compounds of the present invention can be provided as pharmaceutically acceptable compositions or formulations using formulation methods known to those of ordinary skill in the art. These compositions or formulations can be administered by standard routes. In general, when used to treat cell proliferative disorders, the dosage of the compounds will depend on the type of tumor, condition being treated, the particular compound being utilized, and other clinical factors such as weight, condition of the human or animal, and the route of administration. It is to be understood that the present invention has application for both human and veterinarian use.

Any of these compounds can also be used to provide diagnostic information regarding the tumors. For example, if a patient is having a biopsy of his/her tumor, a dose of FAU or related compound can be administered, with or without the use of a radiolabeled atom, or more preferably a stable isotope of the naturally occurring atom, and the DNA from the biopsies treated as in the cell culture experiments.

Any generally known and acceptable radioisotopes or stable isotope of a naturally occurring atom can be utilized in the present invention. However, $^{14}C$ and $^{3}H$ are preferred radioisotopes and stable isotopic labels such as $^{13}C$, $^{2}H$, or $^{15}N$ are most preferred.

Similarly, external imaging, e.g., via positron emission tomography (PET), can be used in particular to detect FAU or related compounds labeled with $^{11}C$ and/or $^{18}F$. By extension from the work shown in cell culture, high levels of FAU incorporation into DNA predicts for successful therapy with FAU or related compounds. Low levels of FAU in DNA suggest that an alternative therapy should be used. Thus, the present invention provides a method for assessing the adequacy of treatment of tumor with various modalities, including thymidylate synthase inhibitors, comprising administering a uridine analogue which is labeled with a position emitter such as $^{11}C$ or more preferably $^{18}F$ and determining the extent of maximum TS inhibition and persistence of TS inhibition over time between doses by external imaging preferably with position emission tomography. These parameters can be used to guide timing of subsequent doses or to determine when current therapy is no longer successful and it is necessary to switch to an alternative therapy.

In preferred embodiments for imaging applications, W may be a label containing moiety or a label. The label may be any moiety that permits the detection of the nucleoside analogue. In preferred embodiments, the label includes a positron emitting atom and in a most preferred embodiment, W is $^{18}F$. In other preferred embodiments for imaging applications, E may be H or methyl. In a most preferred embodiment for imaging, W is $^{18}F$ and E is methyl or H. However, other embodiments are within the scope of the present invention.

It is not necessary for the nucleosides used in imaging applications to be activated by TS. In certain embodiments, the bases of the nucleosides will be 5-methyl deoxyuridine analogues (i.e. thymidine analogues). By providing the nucleoside with a methyl group at the 5-position, one biosynthetic step required for incorporation of the nucleoside into DNA is eliminated. This may have the effect of speeding incorporation into the target DNA and thus providing a better imaging results since the nucleosides should be incorporated more efficiently. In a preferred embodiment, the nucleoside used for imaging will be FMAU wherein the fluorine atom at the 2'-position will be $^{18}F$. Nucleosides having other modifications at the 5-position of the base may be used in imaging applications. For example, the 5-position of the base may be modified to include an iodine atom. Thus, in a preferred embodiment, the nucleoside will be FIAU and the fluorine atom at the 2'-position will be $^{18}F$. Any other modifications at the 5 position of the base may be used in the practice of the imaging applications of the present invention. In preferred embodiments, the nucleoside can serve as a substrate for the enzymes required for incorporation of the nucleoside into DNA thus, the nucleoside will have a 5'-hydroxyl group that can be phosphorylated to the nucleoside triphosphate and the resultant triphosphate can serve as a substrate for the cellular DNA polymerase enzymes.

Also, in the case of biopsy specimens, labeled IdUrd can be administered and interpreted in terms of the cell culture data: high levels of dehalogenation predicts for successful therapy with FAU or related compounds; low dehalogenation suggests that alternative therapy should be used. Thus, the present invention also provides a method of diagnosing tumors which are resistant to thymidylate synthase inhibitors by administering IdUrd which has been labeled with either a radioisotope such as $^{14}C$ or $^{3}H$, or more preferably, with a stable isotopic label such as $^{13}C$, $^{2}H$, or $^{15}N$; preparing biopsy specimens of the tumor; and determining the extent of dehalogenation of IdUrd by thymidylate synthase enzymes by examination of DNA of the tumor specimens. Based upon these results, a therapy regimen can be suggested.

For oral administration, a dosage of between approximately 0.1 to 300 mg/kg/day, and preferably between approximately 0.5 and 50 mg/kg/day is generally sufficient. The formulation may be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association, the active ingredient with liquid carriers or finely divided solid carriers or both, optionally with one or more accessory ingredients, and then, if necessary, shaping the product.

Preferred unit dosage formulations are those containing a daily dose or unit, daily sub-dose, or an appropriate fraction thereof, of the administered ingredient. It should be understood that in addition to the ingredients particularly mentioned herein, the formulations of the present invention may include other agents conventional in the art. It should also be understood that the compounds or pharmaceutical compositions of the present invention may also be administered by topical, transdermal, oral, rectal or parenteral (for example, intravenous, subcutaneous or intramuscular) route or may be incorporated into biodegradable polymers allowing for the sustained release of the compound, the polymers being implanted in the vicinity of the tumor or where the drug delivery is desired.

Figure 1:
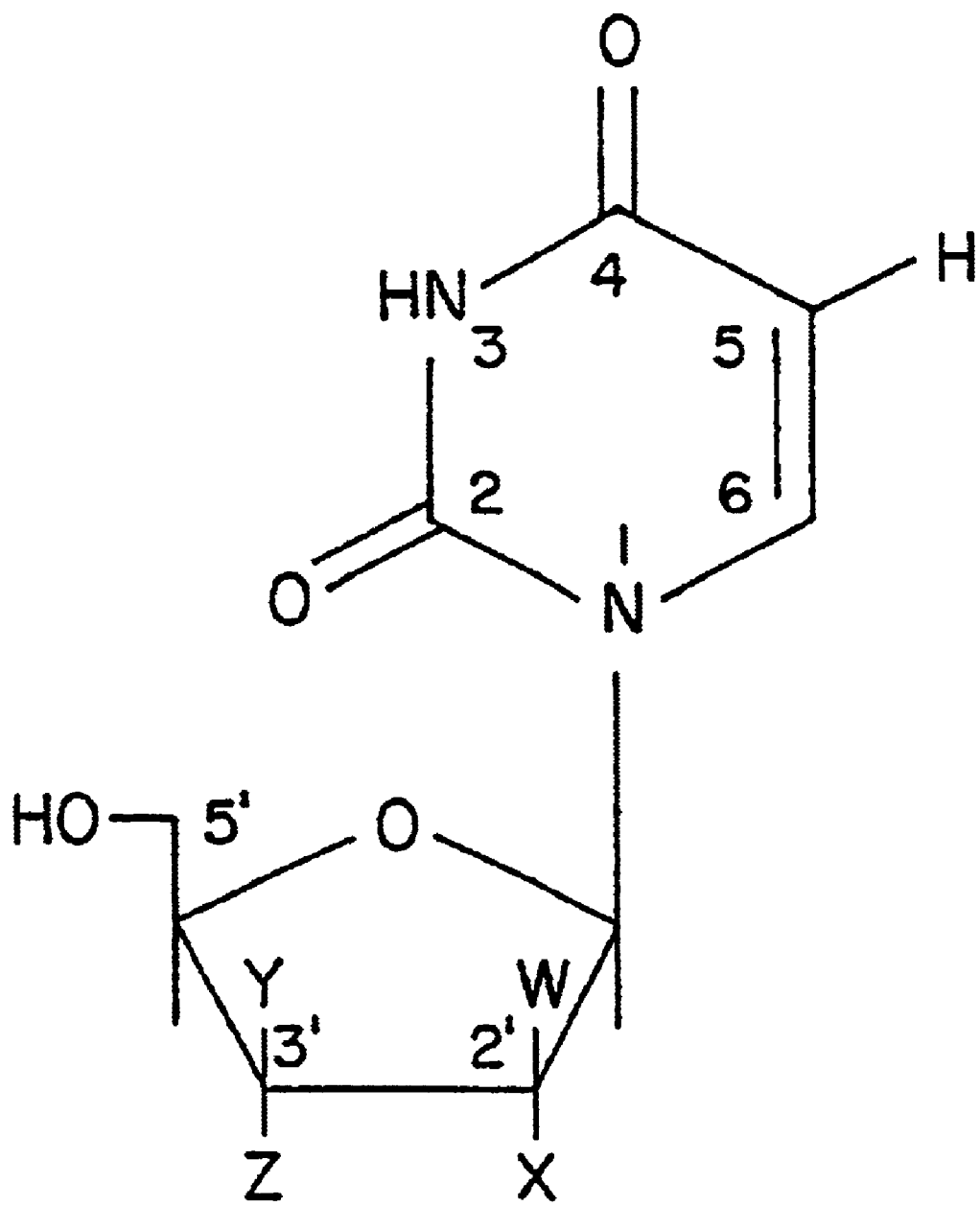
FIG. 1 depicts the general structure for many TS substrates. For the endogenous nucleoside, dUrd, W=X=Y=H, and Z=OH. FAU has only a single substitution, W=F. A phosphate group attached to the sugar at the 5'-position is also required. The corresponding thymidine analogues have a methyl group (—CH$_3$) at the 5-position of the uracil base.

FIG. 1 shows the general structure of many uridine analogues. The base consists of uracil or various modifications. The interaction with TS occurs at the 5-position, where the hydrogen atom is replaced by a methyl group. The endogenous substrate for TS, 2'-deoxyuridine-5'-monophosphate (dUMP), is transformed to thymidine monophosphate (dTMP). The original class of TS inhibitors, 5-fluorouracil (FUra) and 5-fluorodeoxyuridine (floxuridine, FdUrd), after intracellular conversion into FdUMP, form a ternary complex with TS and block the endogenous conversion of dUMP to dTMP. Rather than attempting to block the 5-position as with FUra and FdUrd, the present invention preserves the hydrogen at the 5-position, encouraging the acceptance of the methyl donation. Thus, for those deoxyuridine analogues which are less toxic than the corresponding thymidine analogues, TS can increase cytotoxicity. Analogues may consist of modifications of the base, sugar, or both. The phosphate group at the 5'-position of the sugar is usually added intracellularly (e.g., via thymidine kinase), but modified phosphate groups may be preformed and enter the cell intact (e.g., phosphorothiates or HPMPC).

Several modifications of the bases are feasible. The hydrogen at position 5 and the double bond connecting carbons 5 and 6 are the most essential requirements in the base for the most preferred TS substrate. The nitrogen at position 1 is also a preferred embodiment, however it could be replaced by a carbon, e.g., attempting a more stable linkage with the sugar. The hydrogen attached to N3 can also be replaced with several functional groups, including a halogen, acyl or alkyl substituent. The carboxyl at C2 or C4 can be replaced with a sulfur, as in 4-thiodeoxyuridine.

A phospho-sugar (or sugar analogue) must be attached to the base in order to interact with TS. Many changes to the sugar are possible while still remaining a substrate for TS. In our prototypical compound, F replaces the hydrogen atom at the 2'-position "above" the plane of the sugar (2'-F-arabino), i.e., W=F. The resulting compound, FAU, has been demonstrated to be phosphorylated and converted to its methylated form, FMAUMP. F can also be placed below the ring at the 2'-position, X=F. Bulkier substituents at the 2'-position are synthetically possible, e.g., as reported by Verheyden JPH, Wagner D, and Moffatt J G in "Synthesis of Some Pyrimidine 2'-Amino-2'-deoxynucleosides" in *J. Org. Chem.* Vol 36, pages 250–254, 1971. W=OH yields uracil arabinoside, the main circulating metabolite of ara-C. Compounds substituted in the 3'-position above the ring, Y, have been synthesized, e.g., as reported by Watanabe K A, Reichman U, Chu C K, Hollenberg D H, Fox J J in "Nucleosides. 116. 1-(beta-D-Xylofuranosyl)-5-fluorocytosines with a leaving group on the 3' position. Potential double-barreled masked precursors of anticancer nucleosides" in *J Med Chem* 1980 October; 23(10):1088–1094. Below the ring at the 3'-position, Z=F produces an analogue of fluorothymidine, an antiretroviral agent. A successful antiviral drug, 3'-thiacytidine (3TC) is based upon replacement of the 3'-carbon with a sulfur atom, with no substituents attached above or below the ring. Another reported change in the sugar is the replacement of the oxygen atom with carbon, to form a carbocylic structure, e.g., Lin TS, Zhang X H, Wang Z H, Prusoff W. H., "Synthesis and Antiviral Evaluation of Carbocyclic Analogues of 2'-Azido- and 2'-Amino-2'-deoxyuridine", *J Med Chem* 31:484–6, 1988.

In addition to the set of single substitutions, multiple substitutions would also be included within the scope of the present invention. If both hydrogen atoms at the 2'-position are replaced with F, the resulting molecule is 2', 2'-difluoro-deoxyuridine, which is the main circulating metabolite from gemcitabine, 2', 2'-difluoro-deoxycytidine.

Subsequent to methylation by TS, analogues with modifications to the sugar at the 2'-position can be recognized by DNA polymerases and compete with thymidine triphosphate (dTTP) for incorporation into DNA. If the 3'-OH is preserved (Z=OH), additional bases can be added subsequently. However, if Z is not —OH, then the analogue will serve as a terminator of chain growth. Both chain terminators (e.g., AZT) and non-terminators (e.g., IdUrd) have biological activity, but the spectrum of effects can be quite different.

Acyclic sugar analogues such as acyclovir or cidofovir (HPMPC) have biological activity. In the case of acyclovir and related molecules (such as ganciclovir), a viral form of thymidine kinase is able to phosphorylate the drug despite the altered geometry. For HPMPC, the phosphate group is already present.

Having described the invention, the following examples are given to illustrate specific applications of the invention. These specific examples are not intended to limit the scope of the invention described. It is to be clearly understood that resort may be had to various other embodiments, modifications, and equivalents thereof which, after reading the description herein, may suggest themselves to those skilled in the art without departing from the present invention and/or the scope of the claims.

EXAMPLES

Materials And Methods

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Chemicals

Non-labeled and labeled FAU,. FMAU, FAUMP and dUMP were obtained from Moravek Biochemicals, Brea, Calif. Radio labeled [2-$^{14}$C]FAU; [$^3$H-CH$_3$]FMAU, [5-$^3$H]FAUMP, and [5-$^3$H]dUMP had specific activities of 0.056, 0.33, 11 and 2 Ci/mmol respectively. Deoxyribonuclease I (DNase I) from bovine pancreas, Type II, and phosphodiesterase I from Crotalus atrox, Type VI, formaldehyde, tetrahydrofolate, 2'-deoxyuridine (dUrd), thymidine (dThd), uracil arabinoside (ara-U), and thymine arabinoside (ara-T) were obtained from Sigma Chemical Co., St. Louis, Mo. All other reagents were analytical grade.

Cells

The human-derived cell lines CEM, MOLT-4, RAJI, U-937, K-562 and the murine-derived L1210 were purchased from the American Type Culture Collection, Rockville, Md. Cells were grown and maintained as a suspension culture in RPMI 1640 medium containing L-glutamine and 10% (v/v) heat-inactivated fetal calf serum (BRL-GIBCO, Rockville, Md). Penicillin-streptomycin solution (Sigma Chemical Co., St. Louis, Mo.) was added to achieve a final concentration of 100 units/mL. and 100 μg/mL respectively.

Methylation of FAUMP by Thymidylate Synthase in Cell Extracts

Figure 5:
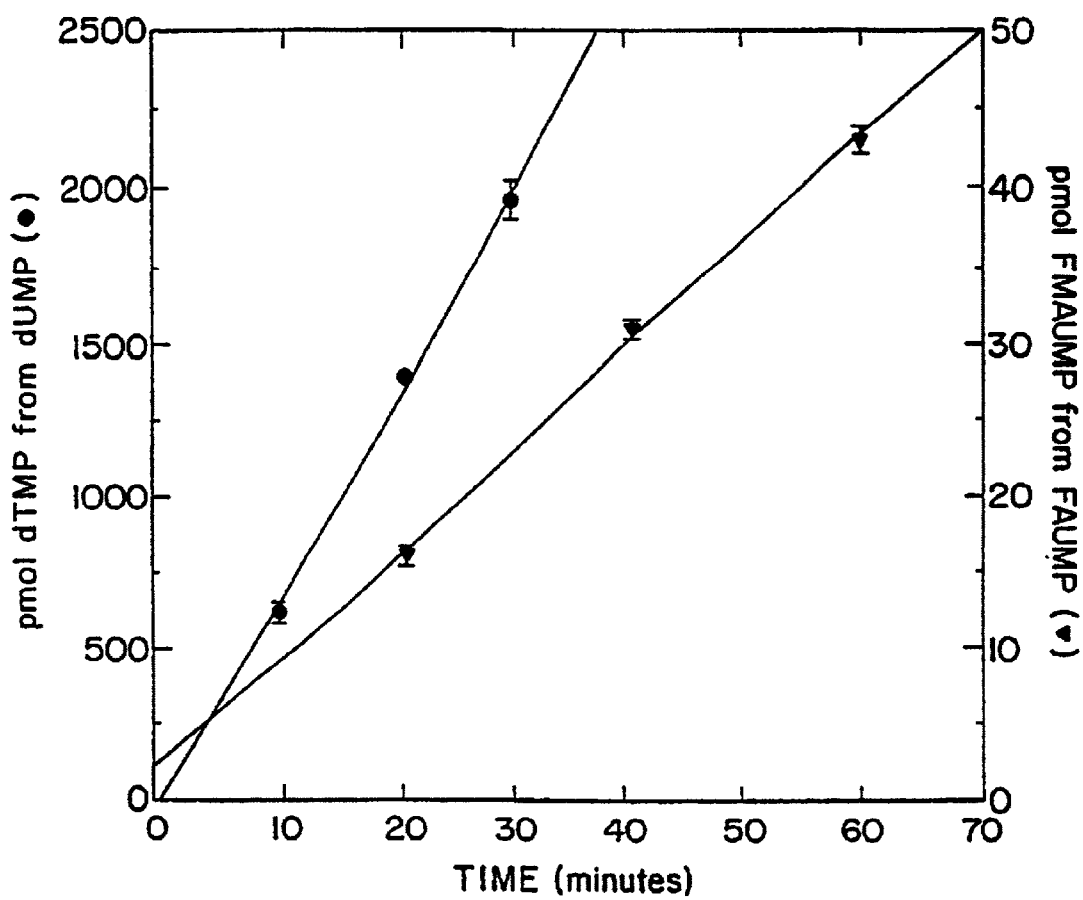
FIG. 5 graphically depicts FAUMP conversion to FMAUMP by TS in U-937 cell extracts, as demonstrated by the accumulation of tritiated water. The rate of conversion to FMAUMP was about 1% of the rate of dTMP formation from dUMP. Similar results were obtained for the other cell lines, with a range of 0.97–1.5%.

When TS adds a methyl group to the 5-position of dUMP to generate dTMP, the proton at that location is released. When [5-$^3$H]dUMP is the substrate, TS activity in cell extracts can be assessed by monitoring the accumulation rate of tritiated water. Here, [5-$^3$H]FAUMP was used as the substrate for methylation by TS, and the generation of FMAUMP was determined from the release of tritiated water. Cell extracts were prepared from each cell line by sonication of intact cells. (See: Armstrong R D, Diasio R B. "Improved Measurement of Thymidylate Synthetase Activity by a Modified Tritium-Release Assay" *J. Biochem. Biophys. Methods.* 1982; 6: 141–7 and Speth P A J, Kinsella T J, Chang A E, Klecker R W, Belanger K. Collins J M. "Incorporation of Iododeoxyuridine into DNA of Hepatic Metastases Versus Normal Human Liver" *Clin. Pharmacol. Ther.* 1988; 44:369–75.) The methyl donor was provided by 5,10-methylene tetrahydrofolate, which was generated in situ by the addition of formaldehyde to tetrahydrofolate. At various times after the addition of substrate (20 μM of either [5 $^3$H]dUMP or [5-$^3$H]FAUMP), the reaction was stopped by addition of HCl. Unreacted substrate was separated from tritiated water by adsorption onto activated charcoal. After centrifugation, an aliquot of the supernatant was counted for tritiated water. As shown in FIG. 5, TS in cell extracts is capable of methylating FAUMP and releasing tritiated water, albeit at a slower rate than for dUMP.

Growth Inhibition Studies

All cell lines, except for L1210, were suspended in fresh media at 30,000 cells/mL. L1210 cells were suspended at 10,000 cells/mL. Cells, 2 mL, were added to each of the wells of 24-well plates and incubated with either 0 to 1000 μM of FAU or 0 to 300 μM of FMAU. Incubation was conducted at 37° C. in a humidified 5% $CO_2$ atmosphere for 72 hours. Inhibition of cellular growth was assessed by cell counting (Elzone 180, Particle Data, Inc., Elmhurst, Ill.). Under these conditions, the control doubling times for CEM, MOLT-4, RAJI, U-937, and K-562 cells were 21–22 hours, while the doubling times for L1210 was 8–10 hours.

Intracellular Nucleotide Formation and Incorporation Into DNA

All cell lines, except for L1210, were resuspended in fresh media at 300,000 cells/mL with appropriate amount of radioactive drug. L1210 cells were resuspended at 150,000 cells/mL. After 24 hours at 37° C. in a humidified 5% $CO_2$ atmosphere, cells were harvested for nucleotide measurement and DNA incorporation. Soluble nucleotides were determined for each cell line following exposure to 10 μM FAU. Incorporation of FAU into DNA (as FMAU) was determined over a range of FAU concentrations from 1 μM to 1 mM. As described previously by Klecker, R W, Katki A G, Collins J M in "Toxicity, Metabolism, DNA Incorporation with Lack of Repair, and Lactate Production for 1-(2'-Fluoro-2'-deoxy-β-D-arabinofuranosyl)-5-iodouracil in U-937 and MOLT-4-cells", *Mol. Pharmacol.* 1994; 46;1204–1209; and Speth PAJ, Kinsella T J, Chang A E, Klecker R W, Belanger K. Collins J M. in "Incorporation of Iododeoxyuridine into DNA of Hepatic Metastases Versus Normal Human Liver." *Clin. Pharmacol. Ther.* 1988; 44:369–75, DNase I and phosphodiesterase I were used to release the bases from DNA. These bases and soluble nucleotides were determined by previously reported HPLC-based methods as noted by Klecker et al. in the previously mentioned reference, "Toxicity, Metabolism, DNA Incorporation with Lack of Repair, and Lactate Production for 1-(2'-fluoro-2'-deoxy-β-D-arabinofuranosyl)-5-iodouracil in U-937 and MOLT-4-cells." Drug incorporation into cellular DNA was determined using the equation: percent incorporation=100×([drug]/([dThd]+[drug]).

Dehalogenation as a Probe for Thymidylate Synthase Activity In Situ. The relative activity of thymidylate synthase was determined after incubation of cells with 3 μM [3H]-IdUrd for 24 hours. DNA was harvested, digested, and chromatographed as described above. Some IdUrd was incorporated into DNA with the iodine remaining intact on the pyrimidine ring. After conversion to IdUMP, part of the IdUrd was dehalogenated by TS to dUMP, which then was converted by TS into dTMP and subsequently incorporated into DNA, and recovered in the DNA digest as [$^3$H-dThd]. Relative TS activity in situ was defined as the fraction of IdUrd-derived material in DNA which was dehalogenated, i.e., ([$^3$H]-dThd)/([$^3$H]-dThd+[$^3$H]-IdUrd). These methods could also be used with non-radioactive IdUrd, if a stable isotopic label is used, e.g., $^{13}$C, $^{15}$N, or $^2$H. A mass spectrometric detector would be substituted for the radioactivity detector in the HPLC analysis. Unlabeled IdUrd can't be used since its dehalogenation produced unlabeled dThd, which would be indistinguishable from the endogenous pool of dThd in DNA.

Example 1

FAUMP was converted to FMAUMP by TS in cell extracts, as demonstrated by the accumulation of tritiated water. The rate of conversion to FMAUMP was about 1% of the rate of dTMP formation from dUMP (FIG. 5). Continuous incubation of cells for 72 hours with the dUrd analogue, FAU, produced varying degrees of growth inhibition (FIG. 2A). At 100 μM, CEM and U-937 cells were more than 50% inhibited, MOLT-4 and K-562 were somewhat less inhibited, but Raji and L1210 cells were completely uninhibited.

Example 2

Continuous incubation of cells for 72 hours with the thymidine analogue, FMAU was more potent and consistently toxic. FMAU produced a concentration-dependent inhibition of growth for all cell lines (FIG. 2B). At the lowest concentration used (0.3 μM), there was a substantial effect on the cell growth of CEM and K-562. At 100 μM all cell lines studied were completely inhibited (>80%). The corresponding deoxyuridine analogue, FAU, was less toxic in all cell lines and had $IC_{50}$ values which were 10-fold higher than with FMAU (FIG. 2A). Most strikingly, the growth of L1210 cells, which were very sensitive to FMAU, was not inhibited by FAU, even at 1 mM.

Both FMAU and FAU were converted intracellularly into FMAU nucleotides, and subsequently incorporated into cellular DNA as FMAU(MP). As described in Table I below, CEM and U-937 cell lines were the most efficient cell lines at forming FMAUTP from FAU and hence FMAU was incorporated to a higher extent into the DNA of these cell lines.

TABLE I

Intracellular Nucleotides Formed and Incorporation into DNA from Incubation of Each Cell Line With 10 µM FAU for 24 Hours.

|  | FAUMP | FMAUTP | DNA |
|---|---|---|---|
|  | nmol/$10^6$ cells |  | % incorp |
| CEM | 0.96 ± 0.24 | 2.30 ± 0.28 | 0.81 ± 0.10 |
| U-937 | 2.70 ± 0.69 | 1.99 ± 0.08 | 0.50 ± 0.02 |
| MOLT-4 | n.d. | 1.92 ± 0.55 | 0.19 ± 0.01 |
| K-562 | 11.1 ± 0.9 | n.d. | 0.22 ± 0.002 |
| RAJI | 0.95 ± 0.17 | n.d. | 0.09 ± 0.002 |
| L1210 | n.d. | n.d. | 0.08 ± 0.005 | n.d. = not detectable

This greater DNA incorporation was reflected as increased toxicity noted for CEM and U-937 in FIG. 2A. In contrast, FAU produced less incorporation of FMAU into the cellular DNA of L1210 cell line. This was reflected as less than 10% decrease in growth rate, even at 1 mM. K-562 cells had a noticeably higher intracellular FAUMP pool. Only trace amounts of FMAUMP or FMAUDP were found.

When cell growth was plotted versus % incorporation of FMAU in DNA (FIG. 3), on the same scale used for extracellular concentration, the response curve was much steeper. Further, the variation among cell lines in IC50 for growth inhibition in toxicity referenced to % incorporation in DNA showed much less variation than when referenced to extracellular concentration. Full curves were obtained for FMAU in all 6 cells lines. For FAU, due to the larger quantities of drug substance which were required, full curves were done in only 2 cell lines, and single points were obtained for the other cell lines.

Example 3

FIG. 4 presents the relative sensitivity of cell lines to growth-inhibition by FAU compared with the activation potential for TS, measured independently as relative dehalogenation of IdUrd. The most sensitive cell lines (U-937, CEM, MOLT-4) have 50% or more dehalogenation. The least sensitive lines (RAJI, L1210) have 15% or lower dehalogenation.

The toxicity of the compounds of the present invention has been evaluated in an animal model system. FAU was administered by oral gavage to mice at a dose of 5 g/kg once per day for 14 consecutive days. After an additional 14 days of observation following this dosing period, the animals were sacrificed. Histopathologic examination of murine tissues found no toxicity attributable to the drug treatment. Blood samples were obtained at various times during this treatment, to confirm that the drug was adequately absorbed. HPLC analysis of these samples indicated FAU concentrations in plasma reached maximum levels of 750 micromolar and minimum levels of 50 micromolar.

Example 4

The present invention includes novel nucleoside analogues useful in imaging technologies as well as methods of synthesizing such analogues. In preferred embodiments, the nucleoside analogue will contain a positron emitting moiety. Such a moiety may be a single atom or a small molecule containing a positron emitting atom. In a most preferred embodiment, the positron emitting moiety will be an $^{18}F$ atom.

The novel nucleoside analogues of the present invention may be prepared by a modification of the procedure reported by Tann C H, et al., "Fluorocarbohydrates in synthesis. An efficient synthesis of 1-(2-deoxy-2-fluoro-alpha-D-arabinofuranosyl)-5-iodouracil (beta-FIAU) and 1-(2-deoxy-2-fluoro-alpha-D-arabinofuranosyl) thymine (beta-FMAU)." *J. Org Chem.* 50:3644–47, 1985, and by the same group in U.S. Pat. No. 4,879,377 issued to Brundidge, et al.

The present method of synthesizing a compound according to the present invention entails contacting a first molecule of the formula

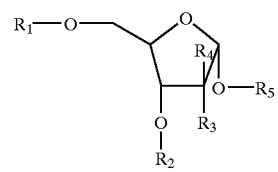

wherein $R_1$, $R_2$ and $R_3$ may be the same or different and are blocking groups, $R_3$ is a leaving group and in preferred embodiments may be triflate, mesylate, tosylate or imidazolsulfonyl, and $R_4$ is H, with a second molecule containing a label under conditions causing the transfer of the label to the position occupied by R4. The resulting labeled compound is brominated at the 1 position and then condensed with a molecule of the formula

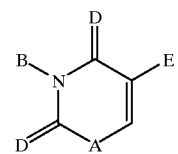

wherein
 A=N, C;
 B=H, hydroxy, halogen, acyl ($C_1$–$C_6$), alkyl ($C_1$–$C_6$), alkoxy ($C_1$–$C_6$);
 D=O, S, NH2;
 E=H, or any substituent which is readily cleaved in the body to generate H.

The synthesis may be initiated with 1,3,5-tri-O-benzoyl-alpha-D-ribofuranoside, which is commercially available, e.g., from Aldrich Chemical Company. This material is modified to generate the precursor for fluorination by addition of an imidazosulfonyl moiety at the 2-position in the ribo-("down") position.

187 mg of 1,3,5-tri-O-benzoyl-alpha-D-ribofuranoside is mixed with 1.54 mL of dry methylene chloride. The mixture is protected from moisture with a calcium chloride or calcium sulfate drying tube while cooling in a salt ice bath to −20° C. Slowly add 70 microliters (110 mg) of sulfuryl chloride through a dropping funnel over 20 minutes. Add 0.44 mL of dry methylene chloride to wash down solids. Imidazole is added in 5 equal portions totaling 10 equivalents (270 mg). Remove the reaction mixture from the cooling bath and let the reaction continue for 2 hours. As the reaction proceeds, the mixture will turn bright yellow.

After washing with water and drying with sodium sulfate, crystallize with hexane at 0–5° C. for 16 hours. The small white crystals are collected, dissolved in boiling acetone and filtered hot. Add boiling water, then allow to crystallize at 4° C. for 16 hours and collect the crystals by centrifugation.

The resultant compound has been shown to be stable for at least several months at room temperature, and can be shipped to the clinical site or regional radiosynthesis center, where it can be stored until needed.

Fluorination Procedure

Because of the short half-life of $^{18}$F (110 minutes), the fluorinated nucleoside must prepared on the day of its clinical use. In these circumstances, the reactions steps are optimized for short times, with yield as a secondary consideration.

On the day of use, 10 mg of the imidazosulfonyl sugar is dissolved in 200 microliters of acetonitrile. $^{18}$F is prepared from a cyclotron in the form of KHF$_2$, and 300 mCi (e.g., combined with 1.32 mg of unlabeled KHF$_2$) is dissolved in 50 microliters of a 1:100 dilution of acetic acid. In the presence of various organic solvents such as diethylene glycol or butanediol, $^{18}$F from KHF$_2$ displaces the imidazosulfonyl moiety on the arabinose ring, and assumes the ara-("up") position. The preferred reaction solvent is 200 microliters of 2,3-butanediol. If a lower volume of solvent is used (more concentrated solution of reactants), the acetic acid is not required. The preferred incubation conditions are 15 minutes at 170° C. This reaction product can be verified with authentic material, available commercially in the non-radioactive form from Sigma Chemical Co. A minimum of 8% yield is formed, based upon $^{18}$F incorporation.

Although imidazosulfonyl is the preferred exchanging group for fluorination, other suitable leaving groups are equivalent for this purpose. Examples of other, suitable groups include, but are not limited to, triflate, mesylate and tosylate can be used instead of the imidazolsulfonyl moiety. The triflate and mesylate versions are readily fluorinated, but the reaction of the tosylate form is less satisfactory. Those skilled in the art will appreciate that other exchanging groups are equivalent for the purposes of the present invention. So long as the exchanging group reaction with the fluorination reagent is fast, efficient and produces minimal side products, any exchanging group known to those in the art is equivalent. Other suitable exchanging groups are disclosed by Berridge, et al. (1986) Int. J. Rad. Appl. Inst. Part A 37(8):685–693.

Alternately, we have have shown that 2-fluoro-2-deoxy-1,3,5-tri-O-benzoyl-alpha-D-arabinofuranose can be formed by direct reaction of underivatized 1,3,5-tri-O-benzoyl-alpha-D-arabinofuranose with DAST, diethylamino-sulfur trifluoride, which can be produced readily with $^{18}$F. The synthesis of $^{18}$F DAST is described by Straatmann, et al. (1977) J. Nucl. Med. 18:151–158.

At the end of the reaction period, 2 mL of methylene chloride are added, followed by 2 mL of water. The methylene chloride layer is transferred to a tube containing 2 mL water. Then, the methylene chloride layer is transferred to another tube and dried under as stream of air or inert gas. Then, 400 microliters of acetonitrile, 100 microliters of acetic acid, and 30 microliters of HBr (30% w/w in acetic acid)are added. The reaction is conducted at 125° C. for 5 minutes, producing a minimum 50 yield of 1-Br-2-F-3,5-di-O-benzoyl-alpha-D-arabinofuranose.

At the end of this reaction step, 1 mL of toluene and 0.5 mL of water are added. The toluene layer is transferred to another tube and dried under a stream of air or inert gas. An additional 0.5 mL toluene is added, and dried. The bromo-fluoro-sugar is "condensed" with a pyrimidine base (e.g., uracil, thymine, iodouracil) in which the 2- and 4-positions have been silylated (e.g., with hexamethyldisilazane), to form bis-trimethylsilyl (TMS) derivatives. TMS-Ura is available commercially, from Aldrich. Other TMS-protected pyrimidine bases (e.g., TMS-Thy, or TMS-IUra)can be prepared prior to the day of use and shipped to the site, as with the imidazosulfonyl sugar. The preparation of TMS-protected bases is described by White, et al. (1972) J. Org. Chem. 37:430. Other suitable protecting groups that can be removed after the reaction in conditions that do not cause a substantial deterioration of the product may be used in place of TMS. The selection of suitable protecting groups and the conditions for their use are well known to those skilled in the art.

200 microliters of a solution of TMS-Ura (or other base) are dried, and 1 mL of methylene chloride is added. The mixture is transferred to the tube containing the fluoro-bromo-sugar. The tube is heated at 170° C. for 15 minutes and then dried, producing a yield of at least 25% of 2,4-di-TMS-3', 5'-di-O-benzoyl-2'-arabino-F-2'-deoxyuridine when TMS-Ura is used.

To remove the blocking groups from the 3'- and 5'-5 positions of the sugar, and the 2- and 4-positions of the base, 0.3 mL of 2M ammonia in methanol is added. The mixture is heated at 130° C. for 30 minutes. The final product, e.g., $^{18}$F-FAU, is purified (e.g., using a solid-phase or liquid extraction cartridge or high-performance liquid chromatography) and prepared for administration in any pharmaceutically acceptable solvent. Any solvent may be used that is safe when administered to a subject so long as the compound is soluble in it. Verification of the identify of the product is obtained by comparison with authentic non-radioactive reference material using any standard technique for chemical identification. For example, FAU and FIAU are available from Moravek Biochemicals (Brea, Calif.). FMAU also available from Moravek by special order (not listed in catalog).

Example 5

The labeled nucleosides of the present invention may be used to evaluate the impact of various treatments upon tumors. Traditionally, most therapies (drugs and/or radiation) were directed towards decreasing tumor growth in a relatively non-specific fashion. More recently, an emphasis has been placed upon approaches such as differentiating the tumor to a slower-growing form and also preventing metastasis of the tumor. For both the traditional approach and newer approaches, a key consideration is early determination of the success or failure of the initial treatment modality, with subsequent treatment modification as necessary. Since all therapies have (substantial) side effects, the penalty for incorrect assessment is two-fold: in addition to the loss of valuable time to find alternative treatment, needless toxicity is endured.

The standard tools for evaluation are often inadequate to provide timely information. A tumor may actually stop growing and the active mass shrink, but this success is masked by the continued presence of non-viable areas, such as necrotic or calcified tissue. Thus, success of the treatment is masked because the tumor doesn't change size by anatomically-based assessments such as X-Ray or CAT scans. Similarly, when the tumor stops responding to therapy and begins to grow, the failure is masked initially because the viable tissue is only a minority of the anatomically-determined lesion.

These problems can be overcome by functional imaging with the labeled nucleosides of the present invention. Imaging methods using compounds of this type are more informative as they have the advantage of focusing only on the viable tissue. This permits the determination of treatment success or failure even in the presence of the "noise" from nonviable tissue.

To image tumors, labeled nucleosides, preferrably labeled with $^{18}$F, are prepared as described above. The compounds can be generally administered to a subject to be imaged at a dose of from about 1 mCi to about 60 mCi. In preferred embodiments, the labeled compounds will be administered in doses of about 1 mCi to about 20 mCi. In a most preferred embodiment, the compounds of the present inventions will be administered in doses of from about 10 mCi to about 20 mCi. The lower limit of the dosage range is determined by the ability to obtain useful images. Dosages lower than about 1 mCi may be indicated in certain instances. The upper limit of the dosage range is determined by weighing the potential for radiation induced harm to the subject against the potential value of the information to be gained. In certain instances, it may be necessary to administer a dosage higher than about 60 mCi.

The radiolabeled compounds of the present invention may be administered in any pharmaceutically acceptable solvent in which they are soluble. In preferred embodiments, the compounds will be dissolved in normal saline or buffered saline. The compounds of the invention may be administered by any route known to those skilled in the art. For example, the administration may be oral, rectal, topical, mucosal, nasal, ophthalmic, subcutaneous, intravenous, intra-arterial, parenteral, intramuscular or by any other route calculated to deliver the compound to the tissue to be imaged. In preferred embodiments the compounds will be administered by intravenous bolus.

Images may be acquired from about 5 minutes after administration until about 8 hours after administration. The maximum period in which images may be acquired is determined by three factors: the physical half-life of $^{18}$F (110 minutes); the sensitivity of the detectors in the imaging machinery; and the size of the dose administered. Those skilled in the art can adjust these factors to permit the acquisition of images at an appropriate time. Blood samples are also generally obtained, to confirm adequate delivery of the administered dose.

Those skilled in the art are capable of using the labeled compounds of the present invention to obtain useful imaging data. Details on imaging procedures are well known and may be obtained in numerous references, for example, Lowe, et al. demonstrate the use of positron emission tomography to analyze lung nodules (J. Clin. Oncology 16:1075–88, 1998) while Rinne, et al. demonstrate the use of an $^{18}$F-labeled probe in imaging protocols to analyze treatment efficacy in high risk melanoma patients using whole-body $^{18}$F-fluorodeoxyglucose positron emission tomography (Cancer 82:1664–71, 1998).

Example 6

The labeled nucleosides of the present invention may be used to assess bone marrow function. Blood cells which are circulating throughout the body have lifetimes ranging from a few days to a few months. Thus, in order to sustain the circulation, blood cells are continuously produced by the body. The primary source of new blood cells is from bone marrow. Normally, bone marrow function can be inferred simply by examining peripheral blood. If the number of blood cells per mL is in the normal range and remaining steady, marrow is working satisfactorily.

In several circumstances, marrow function may have been destroyed, and it is desirable to rapidly and more directly assess the functioning of marrow. Since the production of new blood cells occurs via cell division, DNA synthesis is the key step. Thus, a labeled analogue of thymidine, such as $^{18}$F-FMAU can be used assess marrow function.

One of the circumstances in which it is desirable to rapidly obtain information on the status of the bone marrow is in conventional anticancer chemotherapy. For many antitumor drugs, the bone marrow is substantially damaged, which limits the amount of treatment which can be tolerated by the patient. Thus, initially, blood cell counts drop rapidly after chemotherapy, including loss of the key white blood cells which fight infection. Prolonged loss of these cells creates a serious danger of infections. Generally, the damage is repaired and blood counts return to normal levels within a few weeks. To overcome this delay in recovery of circulating cells, growth factors (e.g., G-CSF, GM-CSF) are administered to patients to stimulate more division among the cells in the bone marrow. As reported by Sugawara, et al. (J. Clin. Oncology 16(1):173–180, 1998), external imaging can provide evidence to show that bone marrow cells are being stimulated. Sugawara, et al. used $^{18}$F-fluorodeoxyglucose as a probe of general energy consumption to assess the state of the bone marrow cells. The use of a thymidine analogue such as $^{18}$F-FMAU would be preferred because it more closely monitors the key event, which is DNA synthesis.

In a more extreme circumstance, a patient'bone marrow is intentionally destroyed with radiation and chemotherapy. After this treatment, the patient receives a "bone marrow transplant", i.e., the marrow which was destroyed is replaced with donor marrow from immunologically-matched individuals, or from a supply harvested from the patient prior to treatment. In either case, the ability of the patient to recover from treatment requires "engraftment", i.e., that the injected cells enter the marrow spaces and begin producing new cells to replace those which have left the circulation. There is very wide variation in the rate at which blood counts recover, so it is critical to determine as early as possible if the engraftment is successful. If failure is detected early, a second bone marrow transplant can be attempted. The longer the wait to determine if blood counts will return, the longer the period of exposure to life-threatening infections.

More recently, marrow function has been restored by transplants from selected peripheral blood cells, known as stem cells. Regardless of whether the source of cells is the marrow or the peripheral circulation, engraftment can be monitored via $^{18}$F-FMAU and similar compounds.

The labeled nucleosides of the present invention can be substituted into the procedure of Sugawara, et al. For example, 1–20 mCi of labeled nucleoside may be administered to a subject. Following administration, sequential dynamic scans may be conducted for 60 minutes following injection. A number of scans of varying duration may be conducted. For example, one protocol that may be used is to conduct six 10-second images, three 20-second images, two 1.5-minute images, one 5-minute image, and five 10-minute images. Those skilled in the art will appreciate that other imaging protocols using varying number and duration of scans may used to practice the present invention.

Example 7

The labeled nucleosides of the present invention may be used to assess the regeneration of liver after surgery. After exposure to injury (chemical, biological, physical, including surgery), the liver is one of the few organs of the body which has the ability to regenerate itself. Hepatocytes begin to replicate themselves to replace lost cells. The most essential element of the regeneration process is synthesis of new DNA molecules. A labeled analogue of thymidine, such as $^{18}$F-FMAU, would be ideal for tracking the rate of regeneration. The short half-life and lower energy of $^{18}$F would be advantages compared with radio-iodine based probes.

Unlike most therapeutic situations, in which a baseline image would be compared with changes induced by treatment, no baseline is typically available in situations in which regeneration is occurring. However, the normal rate of DNA synthesis is very low, so regenerating tissue would be readily detected. For example, Vander Borght, et al. demonstrate in rats that up to 10-fold differences in DNA synthesis can be found in regenerating liver compared with non-regenerating liver demonstrating the feasability of this approach. Vander Borght, et al. used radiolabeled thymidine analogues in a noninvasive measurement of liver regeneration with positron emission tomography (Gastroenterology. 1991 September; 101(3):794–9). Further, the serial evaluation of DNA synthesis with $^{18}$F-FMAU would provide excellent information regarding the stimulation or suppression of regeneration.

The procedure may consist of a bolus intravenous injection of $^{18}$F-FMAU, although other methods of administration may be used. Typically, from about 1 mCi to about 60 mCi of labeled compound may be administered. In preferred embodiments, about 10 mCi may be administered. Based upon the biochemical processes within the liver and the physical half-life of $^{18}$F, the preferred time for image acquisition would be 1–10 hours after the injection. Selecting the timing and duration of the scans is well within the skill of the ordinary practitioner in the art.

Example 8

The labeled nucleosides of the present invention can be used to assess the efficacy of gene therapy applications. One currently used method of gene therapy involves introducing into a cell to be eliminated, a copy of Herpes simplex virus thymidine kinase gene (HSV-tk). The presence of HSV-tk in the cell renders the cell sensitive to the nucleoside analogue ganciclovir. In the presence of ganciclovir, cells expressing HSV-tk are killed while those not expressing the HSV-tk gene are resistant. It has previously been demonstrated by Blasberg, et al. in U.S. Pat. No. 5,703,056 that 2'-fluoro-arabinofuranosyl-nucleoside analogues, FIAU in particular, are specifically phosphorylated by HSV-tk and incorporated into the DNA of cells expressing a functional HSV-tk. Thus, these nucleoside analogues provide a means of assessing the incorporation of HSV-tk into a target cell.

The radiolabeled FIAU disclosed by Blasberg, et al. has several disadvantages. Most notably, radioiodine is a biohazard which persists in the body for many days. The lower energy and shorter half-life of $^{18}$F substantially reduces the biohazard. In clinical situations where the goal is to determine what is happening at the moment, the short half-life of $^{18}$F-FMAU or $^{18}$F-FIAU is a clear advantage compared with radioiodine. This permits the assessment of changes that are occurring on a daily or weekly timescale.

In addition to direct application of thymidine kinase for gene therapy, thymidine kinase can also be used as a "reporter gene" to assess whether the vector (usually a virus) entered the target cells and become functional. This is a particularly important strategy when the function of the primary gene of interest cannot be readily assessed. In this case, observation of thymidine kinase with $^{18}$F-FMAU or related compounds is a surrogate for expression of other genes.

For assessing gene therapy applications, $^{18}$F-labeled nucleosides are prepared as described above. After the gene therapy has been conducted and sufficient time to permit expression of the transduced genes, the subject can be treated with the labeled compounds of the present invention. The compounds can be generally administered to a subject to be imaged at a dose of from about 1 mCi to about 60 mCi. In preferred embodiments, the labeled compounds will be administered in doses of about 1 mCi to about 20 mCi. In a most preferred embodiment, the compounds of the present inventions will be administered in doses of from about 10 mCi to about 20 mCi. The lower limit of the dosage range is determined by the ability to obtain useful images. Dosages lower than about 1 mCi may be indicated in certain instances. The upper limit of the dosage range is determined by weighing the potential for radiation induced harm to the subject against the potential value of the information to be gained. In certain instances, it may be necessary to administer a dosage higher than about 60 mCi.

The radiolabeled compounds of the present invention may be administered in any pharmaceutically acceptable solvent in which they are soluble. In preferred embodiments, the compounds will be dissolved in normal saline or buffered saline. The compounds of the invention may be administered by any route known to those skilled in the art. For example, the administration may be oral, rectal, topical, mucosal, nasal, ophthalmic, subcutaneous, intravenous, intra-arterial, parenteral, intramuscular or by any other route calculated to deliver the compound to the tissue to be imaged. In preferred embodiments the compounds will be administered by intravenous bolus.

Images may be acquired from about 5 minutes after administration until about 8 hours after administration. The maximum period in which images may be acquired is determined by three factors: the physical half-life of $^{18}$F (110 minutes); the sensitivity of the detectors in the imaging machinery; and the size of the dose administered. Those skilled in the art can adjust these factors to permit the acquisition of images at a an appropriate time. Blood samples may also be obtained to confirm adequate delivery of the administered dose.

Specific examples have been set forth above to aid those skilled in the art in understanding the present invention. The specific examples are provided for illustrative purposes only and are not to be construed as limiting the scope of the present invention in any way. All publications, patents, and patent applications mentioned herein are each incorporated by reference in their entirety, for all purposes.

What is claimed is:

1. A method of treating tumors or cancer, comprising: administering a uridine analogue selected by a method comprising the steps of:
   providing a uridine analogue unsubstituted in the 5-position;
   testing said uridine analog for activation by thymidylate synthase; and
   selecting said uridine analog when found to be activated by thymidylate synthase;
   in an effective amount to reduce or inhibit replication or spread of tumor or cancer cells.

2. A method of alleviating cytopathic effects associated with tumors, comprising administering to an afflicted patient an effective amount of a uridine analogue selected by a method comprising the steps of:
  providing a uridine analogue unsubstituted in the 5-position;
  testing said uridine analog for activation by thymidylate synthase; and
  selecting said uridine analog when found to be activated by thymidylate synthase;
  such that said cytopathic effects are alleviated.

3. A composition for reducing or inhibiting the replication or spread of tumor cells, comprising: a uridine analogue selected by a method comprising the steps of:
  providing a uridine analogue unsubstituted in the 5-position;
  testing said uridine analog for activation by thymidylate synthase; and
  selecting said uridine analog when found to be activated by thymidylate synthase;
  and a pharmaceutically acceptable carrier.

4. A method of treating cancer comprising: administering to a cancer patient a therapeutically effective amount of a composition according to claim 3.

5. The composition of claim 3, wherein the uridine analogue is of the following general formula:

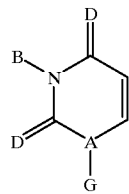

wherein:
  A=N, C;
  B=H, hydroxy, halogen, acyl ($C_1$–$C_6$), alkyl, $C_1$–$C_6$), alkoxy ($C_1$–$C_6$)
  D=O, S, $NH_2$; and
  G=substituted or unsubstituted cyclic sugar, substituted or unsubstituted acyclic sugar, substituted or unsubstituted mono, di, or tri-phospho-cyclic-sugar phosphate; substituted or unsubstituted mono, di, or tri-phospho-acyclic-sugar phosphate; substituted or unsubstituted mono, di, or tri-phospho-cyclic sugar analogues, substituted or unsubstituted mono, di, or tri-phospho-acyclic sugar analogues wherein the substituents are alkyl ($C_1$–$C_6$) alkoxy ($C_1$ to $C_6$), halogen.

6. The method of claim 1, wherein the uridine analogue is selected form the group consisting of FAU, d-Urd and ara-U.

7. The method of claim 1, wherein the uridine analogue is administered to a human or animal in a tumor-inhibiting amount.

8. The method of claim 1, wherein said uridine analogue is administered in combination with other pharmaceutical agents and/or other drugs used to inhibit tumor growth.

9. The method of claim 1, wherein the uridine analogue is of the following general formula:

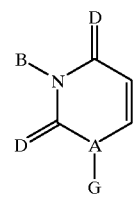

wherein:
  A=N, C;
  B=H, hydroxy, halogen, acyl ($C_1$–$C_6$), alkyl, $C_1$–$C_6$), alkoxy ($C_1$–$C_6$)
  D=O, S, $NH_2$; and
  G=substituted or unsubstituted cyclic sugar, substituted or unsubstituted acyclic sugar, substituted or unsubstituted mono, di, or tri-phospho-cyclic-sugar phosphate; substituted or unsubstituted mono, di, or tri-phospho-acyclic-sugar phosphate; substituted or unsubstituted mono, di, or tri-phospho-cyclic sugar analogues, substituted or unsubstituted mono, di, or tri-phospho-acyclic sugar analogues wherein the substituents are alkyl ($C_1$–$C_6$) alkoxy ($C_1$ to $C_6$), halogen.

10. The method of claim 2, wherein the uridine analogue is of the following general formula:

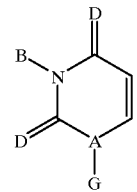

wherein:
  A=N, C;
  B=H, hydroxy, halogen, acyl ($C_1$–$C_6$), alkyl, $C_1$–$C_6$), alkoxy ($C_1$–$C_6$)
  D=O, S, $NH_2$; and
  G=substituted or unsubstituted cyclic sugar, substituted or unsubstituted acyclic sugar, substituted or unsubstituted mono, di, or tri-phospho-cyclic-sugar phosphate; substituted or unsubstituted mono, di, or tri-phospho-acyclic-sugar phosphate; substituted or unsubstituted mono, di, or tri-phospho-cyclic sugar analogues, substituted or unsubstituted mono, di, or tri-phospho-acyclic sugar analogues wherein the substituents are alkyl ($C_1$–$C_6$) alkoxy ($C_1$ to $C_6$), halogen.

11. The method of claim 2, wherein the uridine analogue is selected form the group FAU, d-Urd and ara-U.

12. A method of treating cancer, comprising:
  administering a uridine analog in an amount effective to inhibit the replication or spread of cancer cells, said uridine analog selected by a method comprising the steps of:
    providing a uridine analogue unsubstituted in the 5-position;
    testing said uridine analog for activation by thymidylate synthase; and
    selecting said uridine analog when found to be activated by thymidylate synthase.

* * * * *